(12) United States Patent
Schaller et al.

(10) Patent No.: US 12,144,776 B2
(45) Date of Patent: Nov. 19, 2024

(54) ROBOTIC ANKLE SYSTEM FOR GAIT DISORDER PATIENTS

(71) Applicants: Arizona Board of Regents on Behalf of Arizona State University, Scottsdale, AZ (US); Marcus Schaller, Scottsdale, AZ (US)

(72) Inventors: Marcus Schaller, Gilbert, AZ (US); Wenlong Zhang, Chandler, AZ (US); Seyed Mostafa Rezayat Sorkhabadi, Tempe, AZ (US); Zhi Qiao, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 425 days.

(21) Appl. No.: 17/180,757

(22) Filed: Feb. 20, 2021

(65) Prior Publication Data
US 2021/0259903 A1 Aug. 26, 2021

Related U.S. Application Data

(60) Provisional application No. 62/979,621, filed on Feb. 21, 2020.

(51) Int. Cl.
*A61H 3/00* (2006.01)
*A61F 5/01* (2006.01)
*A61H 1/02* (2006.01)

(52) U.S. Cl.
CPC ............ *A61H 3/00* (2013.01); *A61F 5/0127* (2013.01); *A61H 1/0266* (2013.01);
(Continued)

(58) Field of Classification Search
CPC .......... A61H 3/00–068; A61H 2003/001–065; A61H 1/00; A61H 1/0237–0266;
(Continued)

(56) References Cited

U.S. PATENT DOCUMENTS 3,623,175 A * 11/1971 Emerson ................ A61C 17/32
  185/38
5,035,421 A * 7/1991 Scheller ............... A63B 21/023
  482/79
(Continued)

FOREIGN PATENT DOCUMENTS

CN 107854284 B * 10/2019 ............... A61H 3/00
CN 108505611 B * 11/2020 ............... E03F 7/08
DE 102016105906 A1 * 10/2017

OTHER PUBLICATIONS

Translation of CN 107854284. Accessed from Espacenet on May 17, 2023. (Year: 2019).*
(Continued)

*Primary Examiner* — Valerie L Woodward
*Assistant Examiner* — Paige Kathleen Bugg
(74) *Attorney, Agent, or Firm* — Snell & Wilmer L.L.P.

(57) ABSTRACT

A robotic ankle system provides an assistive force for the heel-up portion of a user gait. Energy is stored in a spring responsive to a heel-on portion of the gait, and then released as the heel-up portion begins. In this manner, the gait of a user is assisted. The systems and methods are of particular use for those affected by stroke or in connection with rehabilitation activities.

20 Claims, 8 Drawing Sheets

(52) U.S. Cl.
CPC ............... *A61F 2005/0158* (2013.01); *A61F 2005/0179* (2013.01); *A61H 2201/1207* (2013.01); *A61H 2201/1642* (2013.01); *A61H 2201/1659* (2013.01); *A61H 2201/5061* (2013.01); *A61H 2201/5097* (2013.01)

(58) Field of Classification Search
CPC ....... A61H 2201/027; A61F 5/01–0195; A61F 2005/0132–0197
USPC .......................................................... 601/5
See application file for complete search history.

(56) References Cited

U.S. PATENT DOCUMENTS

| | | | |
|---|---|---|---|
| 10,537,150 B2* | 1/2020 | Bruel | A63B 25/10 |
| 2002/0094919 A1* | 7/2002 | Rennex | A63B 25/00 |
| | | | 482/124 |
| 2006/0206043 A1* | 9/2006 | Yakimovich | A61F 5/0125 |
| | | | 602/5 |
| 2007/0013185 A1* | 1/2007 | Desmarais | B60R 22/202 |
| | | | 280/801.2 |
| 2013/0046218 A1* | 2/2013 | Wiggin | A61F 5/0127 |
| | | | 602/16 |
| 2020/0163782 A1* | 5/2020 | McDonald | A61H 1/0277 |
| 2020/0268541 A1* | 8/2020 | Sharpes | A61F 5/0125 |

OTHER PUBLICATIONS

Translation of CN 108505611. Accessed from Espacenet on May 17, 2023. (Year: 2020).*
Translation of DE-102016105906-A1. Accessed from Espacenet on Dec. 8, 2023. (Year: 2017).*
P. Mahlknecht, S. Kiechl, B. R. Bloem, J. Willeit, C. Scherfler, A. Gasperi, G. Rungger, W. Poewe, and K. Seppi, "Prevalence and burden of gait disorders in elderly men and women aged 60-97 years: a population-based study," PloS one, Jul. 24, 2013.
D. Lippi, T. Bouras, L. A. Hiemstra, N. K. P. Perera, and S. J. Tulloch, "Knee Surgery, Sports Traumatology, Arthroscopy," Springer, Oct. 12, 2019.
C. M. Kim and J. J. Eng, "The relationship of lower-extremity muscle torque to locomotor performance in people with stroke," Physical therapy, Jan. 2003.
"Gait—Physiopedia, universal access to physiotherapy knowledge."
P. DeVita, J. Helseth, and T. Hortobagyi, "Muscles do more positive than negative work in human locomotion," The Journal of experimental biology, Oct. 2007.
H.P. Crowell, P. Harrison, A. C. Boynton, and M. Mungiole, "Exoskeleton Power and Torque Requirements Based on Human Biomechanics," Defence Technical Information Center, Nov. 2002.
M. B. Yandell, J. R. Tacca, and K. E. Zelik, "Design of a Low Profile, Unpowered Ankle Exoskeleton That Fits Under Clothes: Overcoming Practical Barriers to Widespread Societal Adoption," IEEE transactions on neural systems and rehabilitation engineering: a publication of the IEEE Engineering in Medicine and Biology Society, Apr. 2019.
M. B. Wiggin, G. S. Sawicki, and S. H. Collins, "An exoskeleton using controlled energy storage and release to aid ankle propulsion," IEEE . . . International Conference on Rehabilitation Robotics: [proceedings], 2011.
K. A. Shorter, G. F. Kogler, E. Loth, W. K. Durfee, and E. T. Hsiao-Wecksler, "A portable powered ankle-foot orthosis for rehabilitation," Journal of rehabilitation research and development, 2011.
J. R. Fletcher and B. R. MacIntosh, "Achilles tendon strain energy in distance running: consider the muscle energy cost," Journal of applied physiology (Bethesda, Md.: 1985), Jan. 15, 2015.

W. Zhang, M. Tomizuka, and N. Byl, "A Wireless Human Motion Monitoring System for Smart Rehabilitation," Journal of Dynamic Systems, Measurement, and Control, vol. 138, No. 11, 2016.
R. A. Bogey, J. Perry, and A. J. Gitter, "An EMG-to-force processing approach for determining ankle muscle forces during normal human gait," IEEE transactions on neural systems and rehabilitation engineering : a publication of the IEEE Engineering in Medicine and Biology Society, Sep. 2005. [Online].
Y. Zhang, R. J. Kleinmann, K. J. Nolan, and D. Zanotto, "Design and Evaluation of an Active/Semiactive Ankle-Foot Orthosis for Gait Training," Design and Evaluation of an Active/Semiactive Ankle-Foot Orthosis for Gait Training—IEEE Conference Publication.
J. N. LaPlante and T. P. Kaeser, "The Continuing Evolution of Pedestrian Walking Speed Assumptions," Institute of Transportation Engineers.ITE Journal, vol. 74, (9), pp. 32-40, 2004.
Okada, Yohei, Fukumoto, Takahiko, Takatori, Katsuhiko, Koji, Hiraoka, and Koichi, "Abnormalities of the First Three Steps of Gait Initiation in Patients with Parkinson's Disease with Freezing of Gait," Parkinson's Disease, Jul. 13, 2011.
J. D. Schaafsma, Y. Balash, T. Gurevich, A. L. Bartels, J. M. Hausdorff, and N. Giladi, "Characterization of freezing of gait subtypes and the response of each to levodopa in Parkinson's disease," Wiley Online Library, Jun. 19, 2003.
K. M. Jacob and R. Paterson, "Surgical Repair Followed by Functional Rehabilitation for Acute and Chronic Achilles Tendon Injuries: Excellent Functional Results, Patient Satisfaction and No Reruptures," Wiley Online Library, Mar. 27, 2007.
N. Olsson, K. Nilsson-Helander, J. Karlsson, B. I. Eriksson, R. Thomée, E. Faxén, and K. G. Silbernagel, "Major functional deficits persist 2 years after acute Achilles tendon rupture," SpringerLink, Apr. 30, 2011.
S. G. Parekh, W. H. Wray, O. Brimmo, B. J. Sennett, and K. L. Wapner, "Epidemiology and outcomes of Achilles tendon ruptures in the National Football League," Foot & ankle specialist, Dec. 2009.
N. H. Amin, A. B. Old, L. P. Tabb, R. Garg, N. Toossi, and D. L. Cerynik, "Performance outcomes after repair of complete achilles tendon ruptures in national basketball association players," The American journal of sports medicine, Aug. 2013.
G. S. Sawicki, C. L. Lewis, and D. P. Ferris, "It pays to have a spring in your step," Exercise and sport sciences reviews, Jul. 2009.
M. Ishikawa, P. V. Komi, M. J. Grey, V. Lepola, and G.-P. Bruggemann, "Muscle-tendon interaction and elastic energy usage in human walking," Journal of applied physiology (Bethesda, Md. : 1985), Aug. 2005.
R. A. Bogey, J. Perry, and A. J. Gitter, "An EMG-to-force processing approach for determining ankle muscle forces during normal human gait," IEEE transactions on neural systems and rehabilitation engineering : a publication of the IEEE Engineering in Medicine and Biology Society, Sep. 2005.
T. P. Andriacchi, J. A. Ogle, and J. O. Galante, "Walking speed as a basis for normal and abnormal gait measurements," Journal of biomechanics, 1977.
Kim, S., & Yu, J. (2015). Changes of gait parameters and lower limb dynamics in recreational runners with achilles tendinopathy. Journal of sports science & medicine, 14 2, 284-9.
S. H. Collins, M. B. Wiggin, and G. S. Sawicki, "Reducing the energy cost of human walking using an unpowered exoskeleton," Nature, vol. 522, No. 7555, pp. 212-215, Jan. 2015.
Mooney, L.M., Rouse, E.J. & Herr, H.M. Autonomous exoskeleton reduces metabolic cost of human walking during load carriage. J NeuroEngineering Rehabil 11, 80 (2014) doi:10.1186/1743-0003-11-80.
J. Hitt, A. Oymagil, T. Sugar, K. Hollander, A. Boehler, and J. Fleeger, "Dynamically Controlled Ankle-Foot Orthosis (DCO) with Regenerative Kinetics: Incrementally Attaining User Portability," Proceedings 2007 IEEE International Conference on Robotics and Automation.
Testco "Ledex® Low Profile Size 2EF/2EC—Push or Pull," 124911-0XX datasheet, 2006.
P. T. Chinimill, S. W. Wachtel, P. Polygerinos, and W. Zhang, "Hysteresis Compensation for Ground Contact Force Measurement (56) References Cited

OTHER PUBLICATIONS

With Shoe-Embedded Air Pressure Sensors," vol. 1: Advances in Control Design Methods, Nonlinear and Optimal Control, Robotics, and Wind Energy Systems; Aerospace Applications; Assistive and Rehabilitation Robotics; Assistive Robotics; Battery and Oil and Gas Systems; Bioengineering Applications; Biomedical and Neural Systems Modeling, Diagnostics and Healthcare; Control and Monitoring of Vibratory Systems; Diagnostics and Detection; Energy Harvesting; Estimation and Identifications; Fuel Cells/Energy Storage; Intelligent Transporation.
Sensor Locations. [Online]. Available: http://seniam.org/. [Accessed: Oct. 30, 2019].

\* cited by examiner

ROBOTIC ANKLE SYSTEM FOR GAIT DISORDER PATIENTS

CROSS REFERENCE TO RELATED APPLICATIONS

This application claims priority to and the benefit of U.S. Provisional Patent Application No. 62/979,621, filed on Feb. 21, 2020, and entitled "Robotic Ankle System for Gait Disorder Patients," which is hereby incorporated by reference in its entirety (but excepting any subject matter disclaimers or disavowals, and except to the extent that the incorporated material is inconsistent with the express disclosure herein, in which case the language in this disclosure shall control).

TECHNICAL FIELD

The present disclosure relates to wearable robotics, for example an ankle-foot orthosis for use in walking.

SUMMARY

Systems and methods for assistive ankle supports are disclosed. In an exemplary embodiment, a robotic ankle system comprises a frame for receiving a shoe of a user, a constant force spring to store energy arising from a step of the user, a locking mechanism to hold the constant force spring in a stored energy position, a solenoid to disengage the locking mechanism, and a battery coupled to the solenoid.

In another exemplary embodiment, a method of assisting the gait of a human comprises coupling, to a shoe of a user, a robotic ankle system; storing, in the robotic ankle system and responsive to a downward force arising by a first step of the user, energy in a constant force spring; detecting, by the robotic ankle system, a beginning of a heel-off event in the gait of the user; and releasing, by the robotic ankle system and responsive to the detecting, energy from the constant force spring to provide an assistive force to the user.

The contents of this section are intended as a simplified introduction to the disclosure, and are not intended to be utilized to limit the scope of any claim.

BRIEF DESCRIPTION OF THE DRAWINGS

With reference to the following description and accompanying drawings.

DETAILED DESCRIPTION

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure.

For the sake of brevity, conventional techniques and components for wearable robotic systems may not be described in detail herein. Furthermore, the connecting lines shown in various figures contained herein are intended to represent exemplary functional relationships and/or physical couplings between various elements. It should be noted that many alternative or additional functional relationships or physical connections may be present in exemplary robotic ankle systems and/or components thereof.

Gait disorders can be attributed to a variety of factors including aging, injury, and neurological disorders. A common disorder involves the ankle push-off phase of an individual's gait, which is vital to their ability to walk and propel themselves forward. During the ankle push-off stage, plantar flexor muscles are required to provide a large amount of torque to propel the heel off the ground; thus, a condition that compromises the strength of these muscles can greatly affect one's walking ability. In order to assist in rectifying these issues, ankle-foot orthoses ("AFO") may be used to provide support to a user's ankle and assist with the force utilized for the heel-up stage.

Those most commonly affected by gait disorders are the elderly, with about 10% struggling from ages 60-69 and more than 60% of people affected aged 80 years and older. In addition to age, neurological and trauma-related injuries can have a significant effect on one's walking ability. For example, having the ability to assist a stroke patient's gait not only improves their ability to walk but can be instrumental in rehabilitation to help them regain locomotion.

Principles of the present disclosure contemplate a robotic AFO for aiding during the heel-up stage. An exemplary embodiment utilizes the user's body weight to extend constant force springs positioned parallel to the calf to replicate the muscular force generated in plantar flexion. The extended spring may be held in place using a ratcheting mechanism which is released with a solenoid during heel up. Via use of an exemplary device, assist during the heel-up stage is provided and reduced activation in the plantar flexor muscles may be achieved.

Principles of the present disclosure focus on systems and methods improve the heel off stage of the gait cycle. With reference now to FIGS. 1A, 1B, 1C, 1D, and 1E, in accordance with an exemplary embodiment, an exemplary robotic ankle system 100 is disclosed. In various exemplary embodiments, robotic ankle system 100 functions using a constant force spring 112 and a ratcheting mechanism that stores energy supplied by the user. The energy released upon heel off, which may be monitored (for example, using shoes capable of measuring ground reaction forces), provides an assistive force to the user when walking.

Figure 1A:
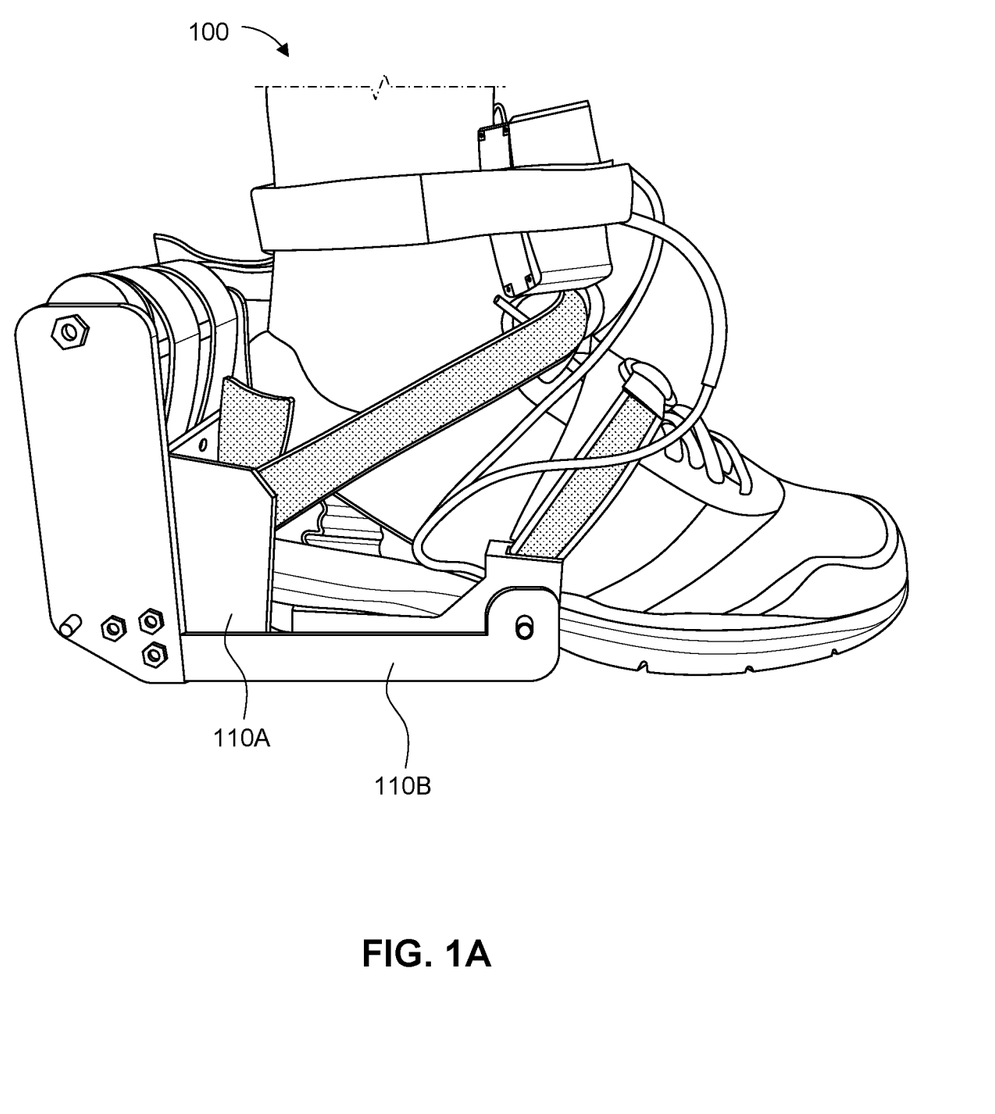
FIG. 1A illustrates an exemplary robotic ankle system in accordance with various exemplary embodiments.
Figure 1B:
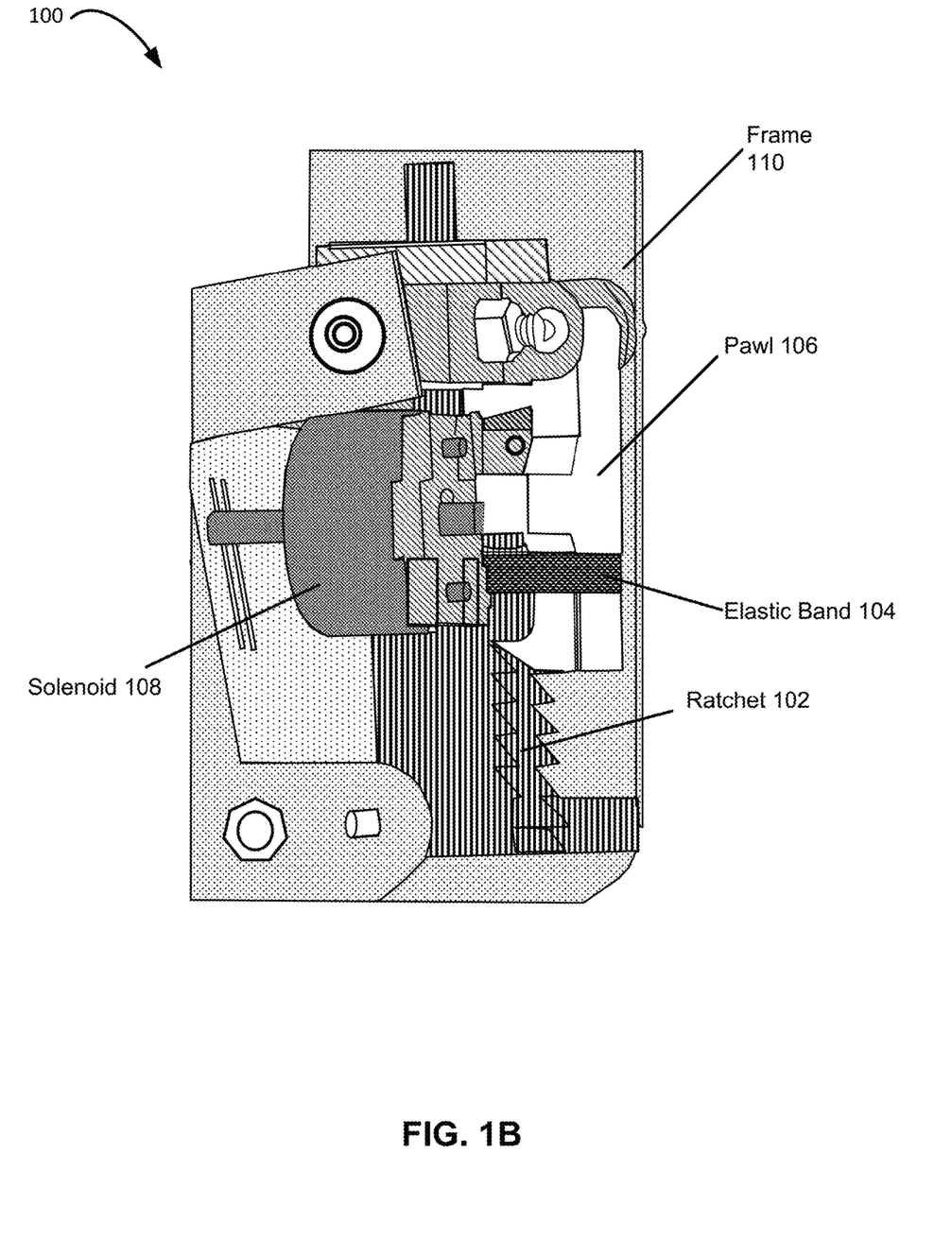
FIG. 1B illustrates components of an exemplary robotic ankle system in accordance with various exemplary embodiments.
Figure 1C:
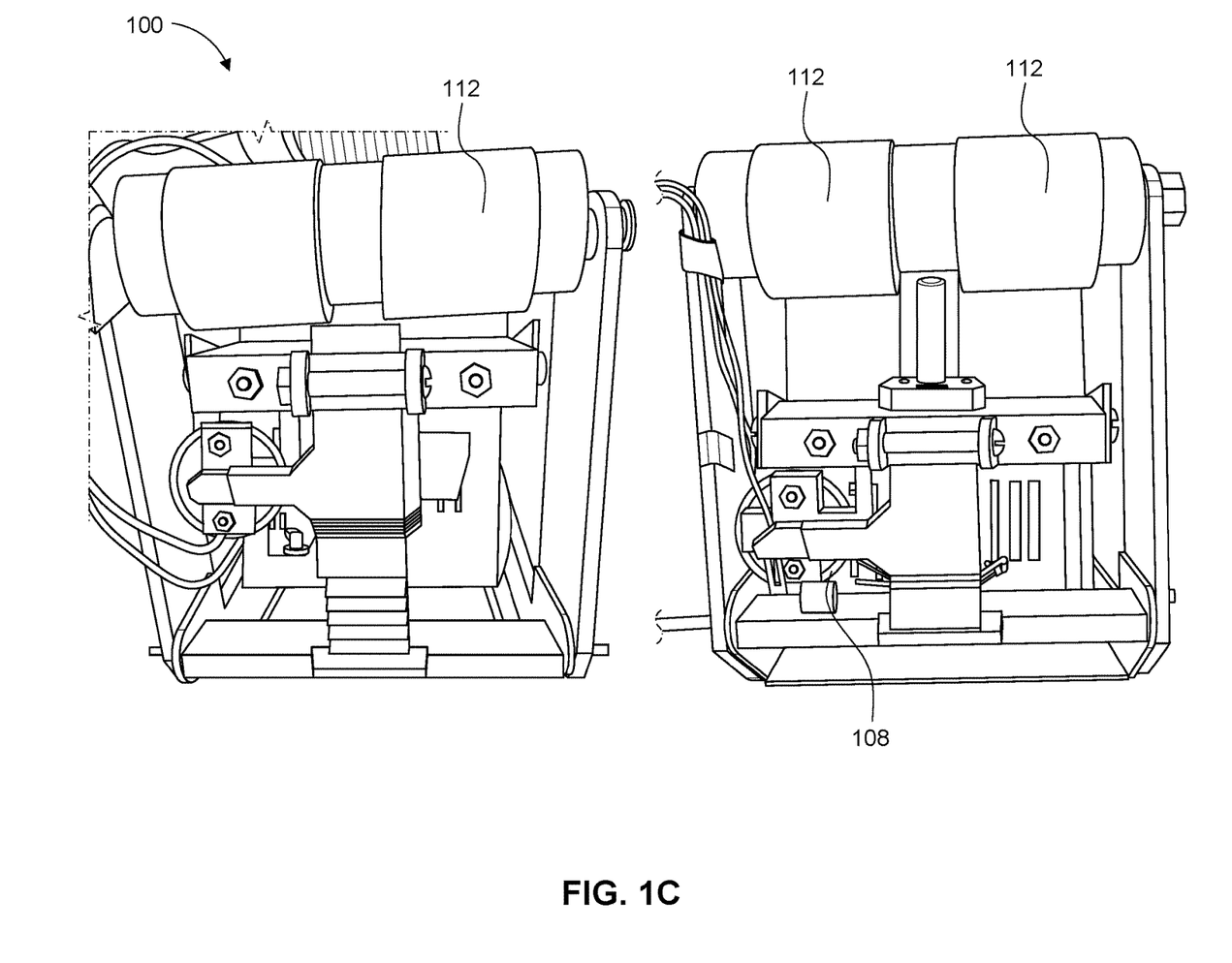
FIG. 1C illustrates an exemplary robotic ankle system in accordance with various exemplary embodiments.

In robotic ankle system 100, a locking mechanism secures a spring 112 in place until release of energy from the spring 112 is desired. In an exemplary embodiment, a locking mechanism is positioned on the back of system 100. This evenly distributes the force throughout the frame 110 to prevent the frame 110 from twisting. In an exemplary embodiment, FIGS. 1B and 1C illustrate how a pawl 106 is held in place with elastic band(s) 104 which pull pawl 106 against ratchet 102. This allows pawl 106 to lock into place without requiring assistance from an actuator. This design helps to reduce power consumption, as the actuator may only utilize power to unlock rather than both for locking and unlocking. The pawl 106 and the ratchet 102 may comprise any suitable materials, for example steel, 6061 aluminum, or other suitable metal so as to increase the longevity of system 100. Moreover, any suitable locking mechanism may be utilized.

The locking mechanism may be released via any suitable approach, for example via operation of a solenoid 108. An exemplary embodiment utilizes a Ledex 2EC push-pull solenoid, which is capable of outputting 30N of pushing force at 3 mm from its extended position. However, any suitable solenoid 108 or other release components may be utilized. In one exemplary embodiment, solenoid 108 is utilized for about 0.36 seconds per gait cycle (about 25% of the total time) and draws about 0.96 amperes of current. Solenoid 108 (and other components of robotic ankle system 100) may be powered via any suitable power source, for example a primary or rechargeable battery coupled thereto and carried by a user, for example on a belt. In some exemplary embodiments, a battery may be integrated into robotic ankle system 100 and/or an associated item of footwear.

Figure 1D:
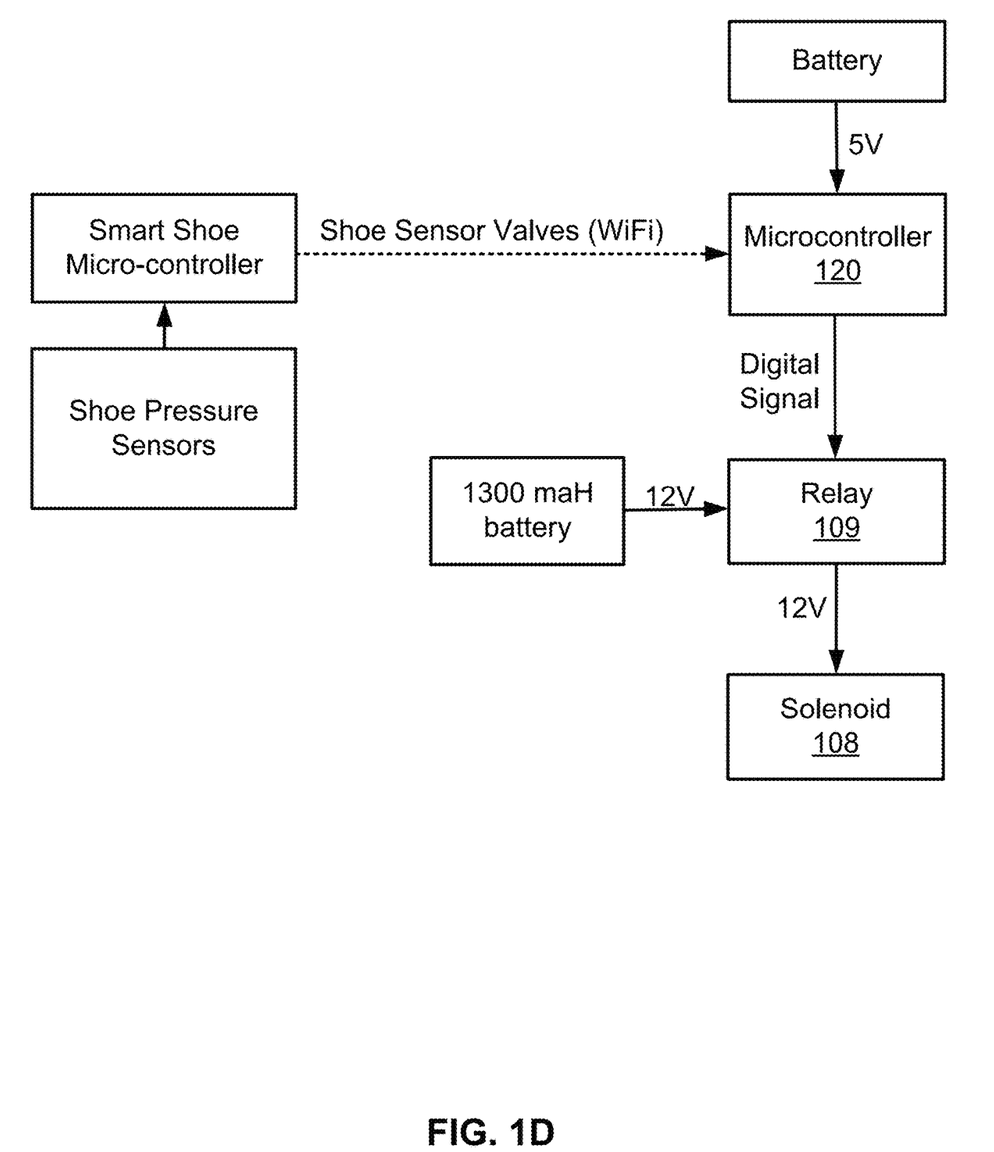
FIG. 1D illustrates a block diagram of components and operation of an exemplary robotic ankle system in accordance with various embodiments.
Figure 1E:
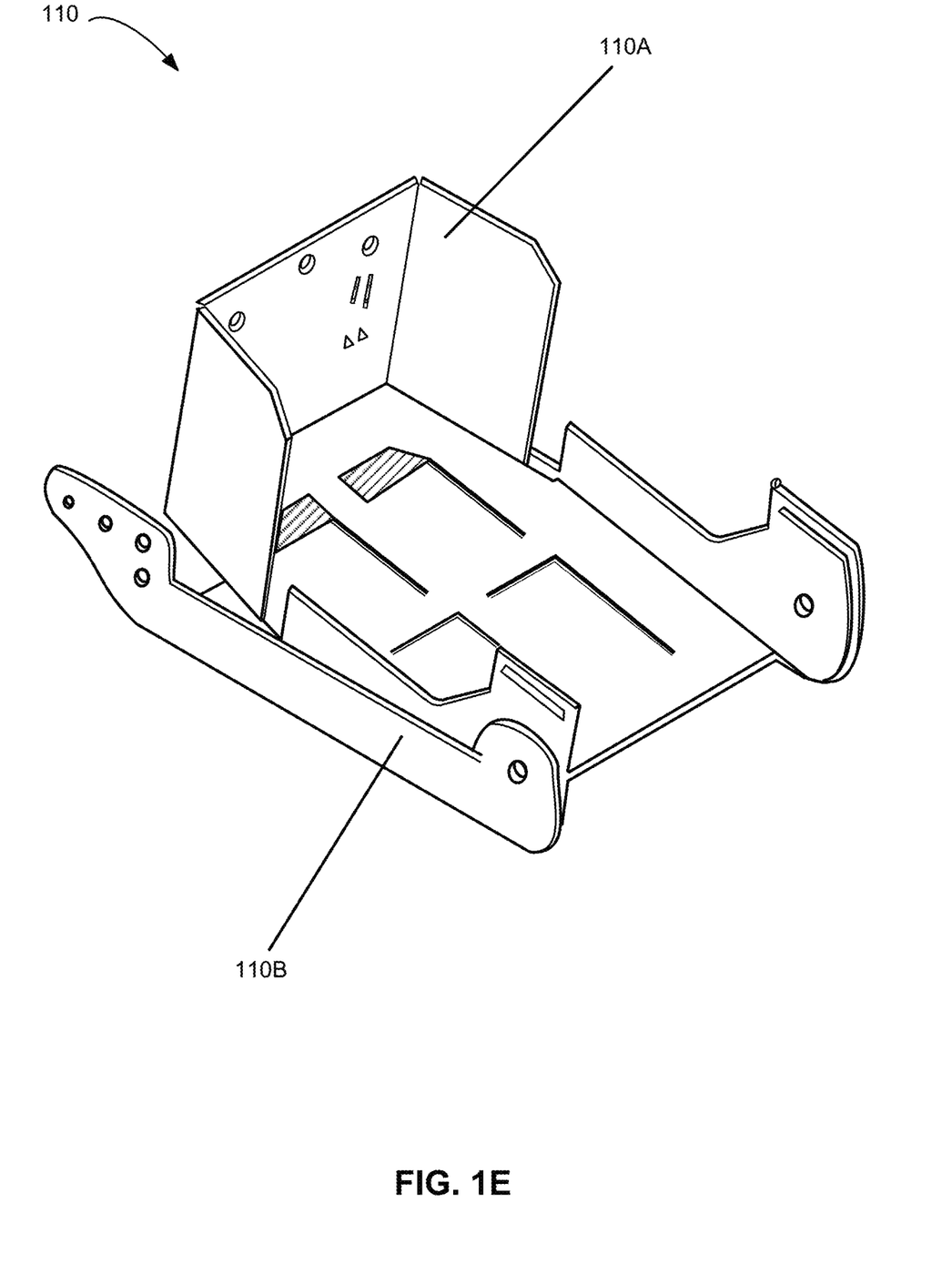
FIG. 1E illustrates a frame of an exemplary robotic ankle system in accordance with various exemplary embodiments.

In various embodiments and with specific reference to FIG. 1E, robotic ankle system 100 utilizes a frame 110, for example in order to receive a shoe of a user. Frame 110 may consist of a foot plate 110A that the foot/shoe is placed into, as well as a base plate 110B. The two plates are made of 5052 aluminum or other suitable durable material, such as steel, and are pivotable with respect to one another as seem in FIG. 1E. In an embodiment, frame 110 is sized to accommodate athletic shoes that are less than 94.675 mm wide or up to men's size 12. However, any suitable frame 110 size (or size of components thereof) may be utilized, for example depending on the weight or shoe size of a user. In various exemplary embodiments, frame 110 has a mass of between about 186 grams and about 541 grams. Moreover, frame 110 may comprise various cut-outs or voids in order to reduce mass while preserving a desired level of rigidity and support for frame 110. In some exemplary embodiments, frame 110 is configured to support a user of up to 90 kilograms in weight while maintaining a maximum deflection for any part of frame 110 of less than 2.24 millimeters, leading to a sturdy feel for a user.

In operation, robotic ankle system 100 extends (or alternatively, compresses) a spring 112 responsive to the weight of a user during a heel-down event, and then releases the spring 112 during a heel-up event. In various exemplary embodiments, a constant force spring 112 is utilized, for example a constant force spring providing between 5 and 10 kg of force, and more particularly about 6.7 kg of force. One or more springs 112 may be utilized, for example two springs, three springs, or more springs. Moreover, the springs may be of varying types, shapes, sizes, materials, or forces, as desired. An exemplary embodiment utilizes two steel strip-style constant force springs 112 having a combined 13.4 kg of force and 17.03 Nm of torque. In total, this accounts for about 11% of torque utilized for a 90 kg user during the corresponding ankle movement.

Through the heel up phase, an exemplary robotic ankle system 100 can do about 4.75 J of mechanical work. A constant force spring 112 may be desirable as it can provide a force throughout the entire heel up gait cycle as compared to a linear spring which would only provide assistance during the initial moments of heel off; however, any suitable spring 112 may be utilized. In addition, a constant force spring 112 allows for improved control systems as the force provided can be easily modeled and/or governed throughout the entire gait cycle. A constant force spring 112 also provides the same amount of force at each of the different locking positions compared to a linear force spring 112 which would not provide as much force when the foot is not fully flat.

Exemplary systems and methods as disclosed herein may be utilized with other systems and methods, for example a smart shoe as set forth in U.S. Ser. No. 16/580,791 filed on Sep. 24, 2019, now U.S. Patent Application Publication No. 2020/0093438 entitled SMART SHOES WITH ADAPTIVE SAMPLING FOR REHABILITATION AND HEALTH MONITORING (the "Smart Shoe App"), the contents of which are hereby incorporated by reference in their entirety (but excepting any subject matter disclaimers or disavowals, and except to the extent that the incorporated material is inconsistent with the express disclosure herein, in which case the language in this disclosure shall control).

In various exemplary embodiments and with particular reference to FIG. 1D, in operation robotic ankle system 100 may be operated as follows: pressure sensor signals from a shoe as disclosed in the Smart Shoe App are collected by a microcontroller on the smart shoe and sent (for example, via wireless signal) to a microcontroller 120 (e.g., a Raspberry Pi or other suitable controller) that is used for control of robotic ankle system 100. Once received by microcontroller 120, the shoe's sensor data may be filtered, for example using a Finite Impulse Response filter routine, to reduce any sensor noise. This filtered data may then be used to determine the pressures at particular locations on the sole of the shoe over time. When a pressure sensed on the heel area of the shoe is lower than a sensed pressure or pressures toward the front of the foot area of the shoe, robotic ankle system 100 may determine that a "heel off" event is beginning; microcontroller 120 sends a signal to a relay 109 controlling a solenoid 108 responsible for the unlock cycle of the ratchet 102 mechanism. Unlatching the ratchet 102 releases the stored energy spring 112 and assists in the upward motion of the heel. After the stored energy spring 112 releases its energy and/or after a suitable time period (for example, between about 400 milliseconds and about 600 milliseconds, and more preferably about 500 milliseconds), microcontroller 120 releases the relay 109 and solenoid 108 in preparation for beginning another gait cycle (storage of energy in spring 112 during heel down→release of energy in spring 112 during heel up). In various exemplary embodiments, robotic ankle system 100 is suitable for use in connection with a walking speed of up to about 0.8 meters per second, and preferentially, about 0.6 meters per second.

Figure 2A:
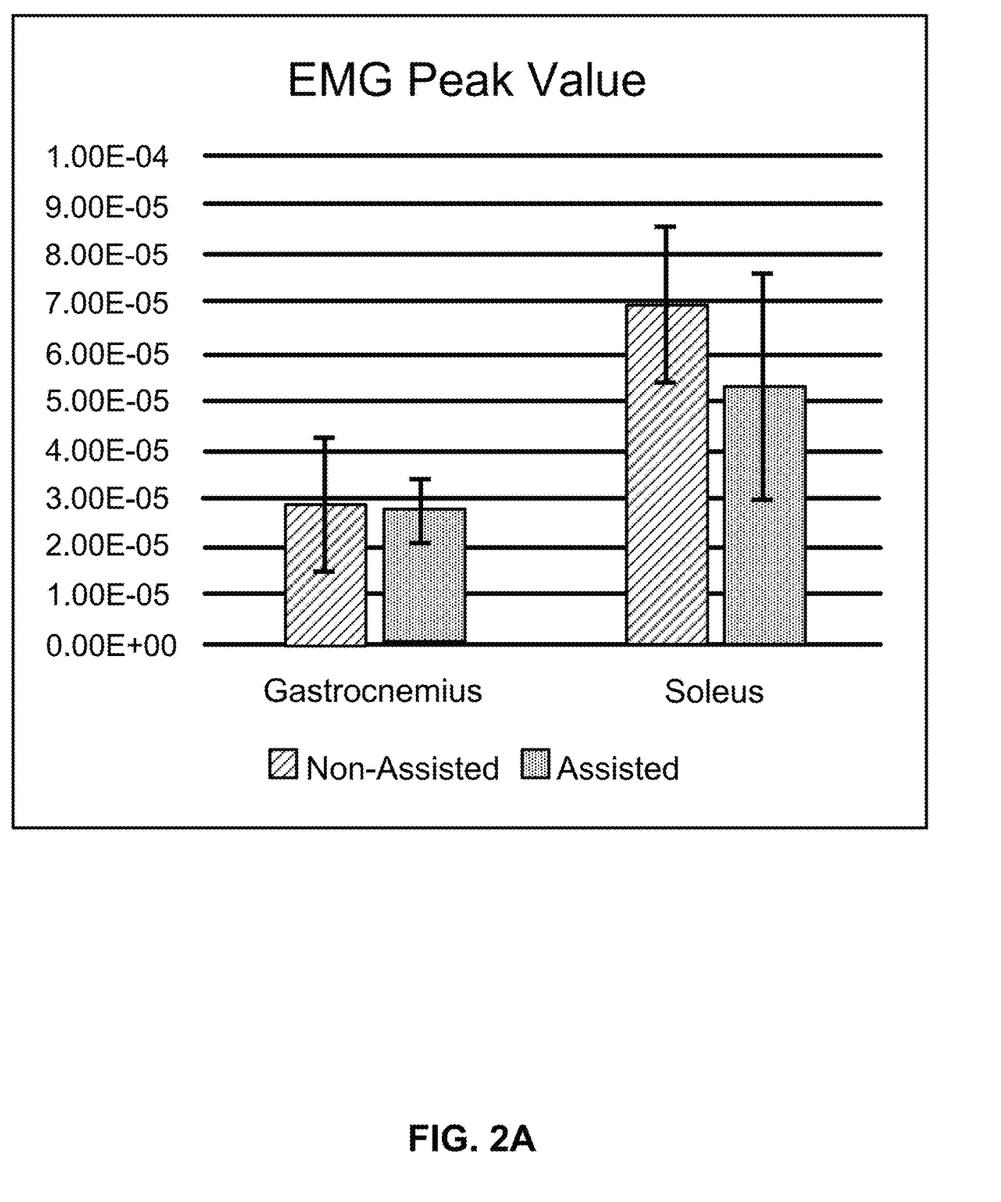
FIGS. 2A and 2B illustrate reduced muscle effort arising via use of an exemplary robotic ankle system in accordance with various exemplary embodiments.
Figure 2B:
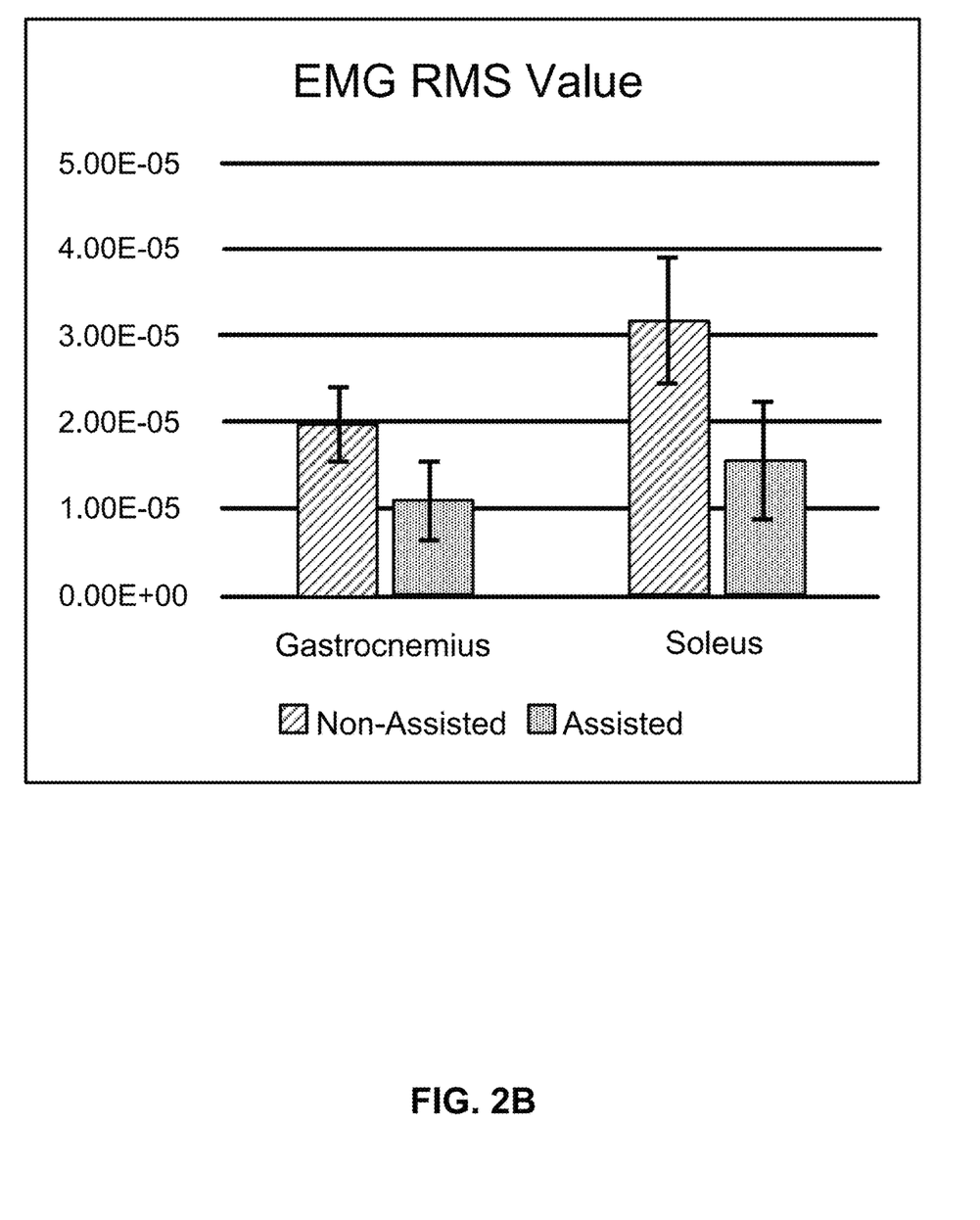

With reference now to FIGS. 2A and 2B, via use of an exemplary robotic ankle system 100, muscle activation may be reduced, providing gait support to the user and resulting in improved mobility and improved locomotion, for example in connection with rehabilitation after a stroke. In an exemplary embodiment, robotic ankle system 100 was tested on an unimpaired 178 centimeter height and 68 kilogram weight male subject, who also wore a US size 10 shoe system as disclosed in the Smart Shoe App. The subject walked on a Bertec dual belt treadmill (Columbus, OH) with integrated force plates. The test was conducted with robotic ankle system 100 present, and again with robotic ankle system 100 absent. The experiments were done at a walking speed of about 0.6 m/s. To measure muscle activities, surface electromyography (sEMG) sensors were placed on the major plantar flexion muscles, the gastrocnemius and soleus. FIGS. 2A and 2B show a reduction of about 5% sEMG peak value in the gastrocnemius muscle and a reduction of about 24% for the Soleus muscle during the assisted walking versus the non-assisted walking trials. The RMS values indicate a reduction in muscular energy expended. Use of robotic ankle system 100 resulted in a reduction was about 30% for the gastrocnemius and about 38% for the soleus. These results demonstrate the efficacy of system 100 and the principles of operation utilized therein.

Figure 3:
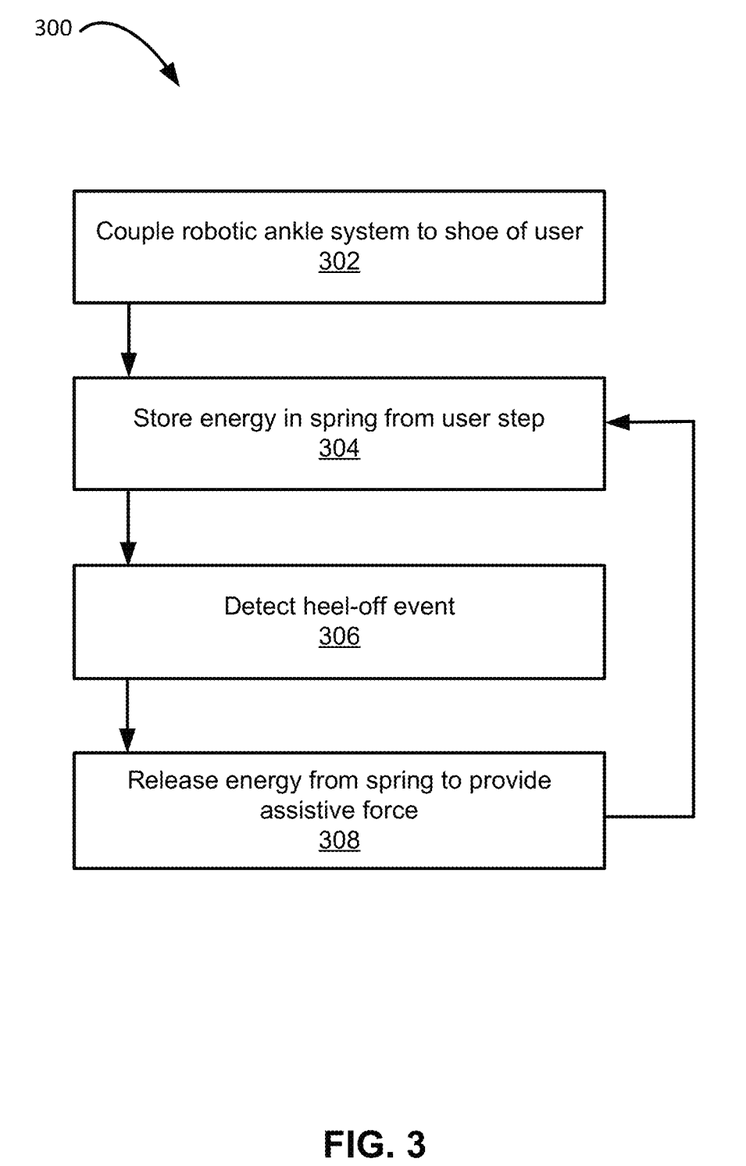
FIG. 3 illustrates a method of using a robotic ankle system in accordance with various exemplary embodiments.

With reference to FIG. 3, in one exemplary embodiment, a method 300 of assisting a gait of a human comprises: coupling, to a shoe of a user, a robotic ankle system (step 302); storing, in the robotic ankle system and responsive to a downward force arising by a first step of the user, energy in a constant force spring (step 304); detecting, by the robotic ankle system, a beginning of a heel-off event in the gait of the user (step 306); and releasing, by the robotic ankle system and responsive to the detecting, energy from the constant force spring to provide an assistive force to the user (step 308). It will be appreciated that steps 304-308 may be repeated as desired as the user walks. Moreover, a robotic ankle system, such as robotic ankle system 100, may be coupled to one foot of a user; alternatively, a user may utilize a robotic ankle system 100 on each foot, and the first and the second robotic ankle system may operate independently.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. When language similar to "at least one of A, B, or C" or "at least one of A, B, and C" is used in the specification or claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A robotic ankle system, comprising:
   a frame configured for receiving a shoe of a user, the frame includes a foot plate and a base plate pivotably coupled to one another at a front end of the foot plate, the foot plate is configured to receive the shoe of the user, a bottom surface of the base plate is configured to contact the ground when the user is walking, the foot plate extends laterally between and to a first side and a second side configured to receive the shoe of the user therebetween, the foot plate further extends longitudinally between and to an aft end and the front end, and the foot plate is configured to pivot with respect to the base plate about an axis that is oriented laterally;
   a constant force spring configured to store energy arising from a step of the user;
   a locking mechanism configured to hold the constant force spring in a stored energy position;
   a solenoid configured to disengage the locking mechanism to release the constant force spring to thereby bias the foot plate to rotate with respect to the base plate to provide an assistive force to the user; and
   a battery coupled to the solenoid.

2. The robotic ankle system of claim 1, further comprising control electronics operative to activate the solenoid and disengage the locking mechanism.

3. The robotic ankle system of claim 2, wherein the locking mechanism comprises a ratchet and pawl, and the solenoid is coupled to the pawl for unlocking the pawl from the ratchet.

4. The robotic ankle system of claim 3, further comprising an elastic band that exerts an engaging force between the ratchet and the pawl.

5. The robotic ankle system of claim 4, wherein the control electronics comprise a wireless communication device in electronic communication with at least two force sensors disposed on the shoe of the user.

6. A method of assisting a gait of a human, the method comprising:
   coupling, to a shoe of a user, a robotic ankle system, wherein the robotic ankle system comprises a frame including a foot plate and a base plate pivotably coupled to one another at a front end of the foot plate, wherein the foot plate receives the shoe of the user, and wherein a bottom surface of the base plate contacts the ground when the user is walking, the foot plate extends laterally between and to a first side and a second side configured to receive the shoe of the user therebetween, the foot plate further extends longitudinally between and to an aft end and the front end, and the foot plate is configured to pivot with respect to the base plate about an axis that is oriented laterally;
   storing, in the robotic ankle system and responsive to a downward force arising by a first step of the user, energy in a constant force spring;
   detecting, by the robotic ankle system, a beginning of a heel-off event in the gait of the user; and
   releasing, by the robotic ankle system and responsive to the detecting, energy from the constant force spring whereby the constant force spring biases the foot plate to rotate with respect to the base plate to provide an assistive force to the user.

7. The method of claim 6, wherein the robotic ankle system further comprises:

the constant force spring to store energy arising from the first step of the user;
a locking mechanism to hold the constant force spring in a stored energy position;
a solenoid to disengage the locking mechanism; and
a battery coupled to the solenoid.

8. The method of claim 7, wherein the locking mechanism comprises a ratchet and pawl, and wherein the robotic ankle system further comprises an elastic band providing an engaging force between the ratchet and the pawl, and wherein the solenoid is coupled to the pawl.

9. The method of claim 8, wherein the detecting comprises:
receiving, at the robotic ankle system, pressure information indicating a first pressure on a sole of the shoe at a heel area;
receiving, at the robotic ankle system, pressure information indicating a second pressure on the sole of the shoe at an area forward of the heel area;
comparing the first pressure and the second pressure; and
when the first pressure is lower than the second pressure, identifying the beginning of the heel-off event.

10. The method of claim 9, wherein the releasing of energy from the constant force spring comprises activating the solenoid to disengage the ratchet and the pawl.

11. The method of claim 9, further comprising:
deactivating the solenoid to allow the ratchet and the pawl to reengage; and
reengaging the ratchet and the pawl after the constant force spring has stored energy responsive to a downward force arising by a second step of the user.

12. The method of claim 6, further comprising:
sending a signal to a relay controlling a solenoid to activate the solenoid to disengage a locking mechanism; and
deactivating the solenoid to allow the locking mechanism to reengage after a predetermined time period.

13. The method of claim 6, wherein the releasing includes sending a signal to a relay controlling a solenoid to activate the solenoid to disengage a locking mechanism.

14. The method of claim 6, wherein the foot plate and the base plate are pivotably coupled to one another at a frontmost side of the frame.

15. The robotic ankle system of claim 2, further comprising at least one shoe pressure sensor configured to measure pressure information indicating a first pressure on a sole of the shoe at a heel area and further indicating a second pressure on the sole of the shoe at an area forward of the heel area, and the control electronics are configured to control the solenoid based upon the pressure information.

16. The robotic ankle system of claim 1, wherein the constant force spring includes two strip-style constant force springs.

17. The robotic ankle system of claim 2, wherein the control electronics are configured to:
activate the solenoid and disengage the locking mechanism for a predetermined time period in response to detecting a beginning of a heel-off event in a gait of the user; and
deactivate the solenoid to reengage the locking mechanism after the predetermined time period.

18. The robotic ankle system of claim 1, wherein the constant force spring is configured to be located behind a heel of the user when the robotic ankle system is worn by the user.

19. The robotic ankle system of claim 1, wherein:
a downward force is applied to the foot plate arising by the step of the user so as to rotate the foot plate downward toward the base plate; and
the constant force spring biases the foot plate to rotate with respect to the base plate to provide the assistive force to the user so as to apply an upward force to a heel of the user to propel the heel of the user upward.

20. The robotic ankle system of claim 1, wherein the foot plate is configured to receive a heel portion of the shoe of the user.

* * * * *